United States Patent [19]

Karin

[11] Patent Number: 4,601,978

[45] Date of Patent: Jul. 22, 1986

[54] MAMMALIAN METALLOTHIONEIN PROMOTER SYSTEM

[75] Inventor: Michael Karin, Los Angeles, Calif.

[73] Assignee: The Regents of the University of California, Berkeley, Calif.

[21] Appl. No.: 444,134

[22] Filed: Nov. 24, 1982

[51] Int. Cl.$^4$ .................... C12N 1/20; C12N 5/00; C12N 5/02; C12N 1/00; C12N 15/00; C12P 21/00; C12P 21/02; C12P 19/34; C07H 21/04

[52] U.S. Cl. .................................. 435/68; 435/70; 435/91; 435/172.3; 435/253; 435/240; 435/241; 435/317; 536/27; 935/6; 935/32; 935/36; 935/70

[58] Field of Search .............. 435/68, 70, 91, 172, 435/253, 317, 240, 241, 172.3; 536/27; 935/32, 36, 6, 70

[56] References Cited

PUBLICATIONS

Karin et al., Nucleic Acids Res. 10, 3165 (1982).
Durnam et al., Proc. Natl. Acad. Sci. USA 77, 6511 (1980).
Pulido et al., Biochemistry 5, 1768 (1966).
Brinster et al., Nature 296, 39 (1982).
Hager et al., Nature 291, 340 (1981).
Karin, Diss. Abstr. 40(9), 4084 (1980).
Douglas R. Lowy, et al,. Nature (1980) 287:72–74.
Ming-Fan Law et al., Proc. Natl. Acad. Sci. USA (1981) 78:2727–2731.
Sarver et al., Preprint of Mol. Cell Biol. (1981).

Primary Examiner—Thomas G. Wiseman
Assistant Examiner—James Martinell
Attorney, Agent, or Firm—Townsend and Townsend

[57] ABSTRACT

A cloning vector comprises a replication system from a bovine papilloma virus, a regulatory system including the promoter and terminator from a human metallothionein II gene, and a prokaryotic replication system. The vector is useful for transforming mammalian cells where it is maintained as an automonously replicating episome. Transcription may be regulated by the presence of heavy metals and/or glucocorticoid hormones in the growth media.

16 Claims, 3 Drawing Figures

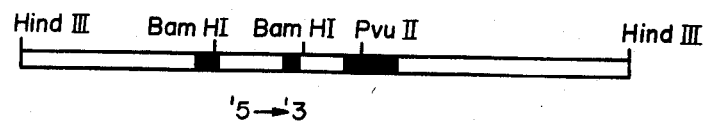
FIG._1
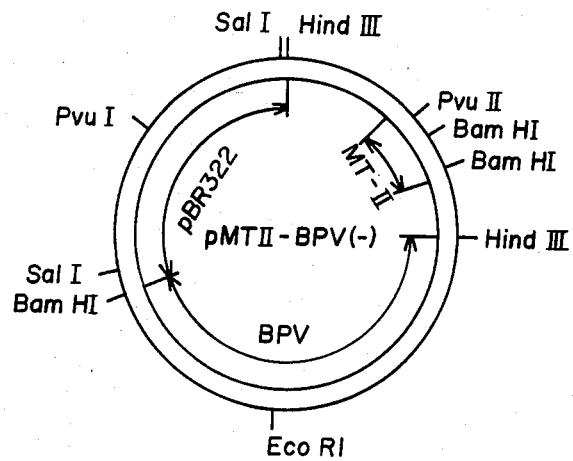
FIG._2
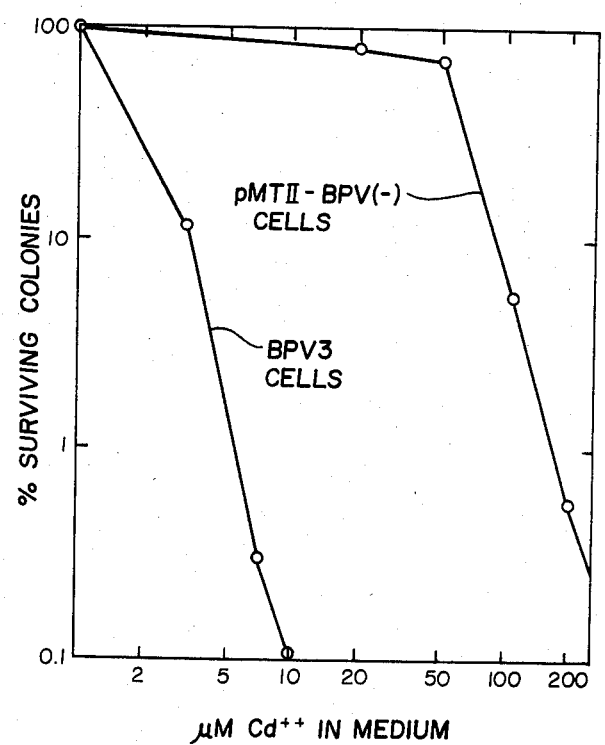
FIG._3

MAMMALIAN METALLOTHIONEIN PROMOTER SYSTEM

This invention was made with Government support under Grant No. R809189 awarded by the Environmental Protection Agency. The Government has certain rights in this invention.

BACKGROUND OF THE INVENTION

1. Field of the Invention

A great deal of interest is now focused on introducing and expressing foreign genes in mammalian cell lines. It is likely that many medically and commercially desirable proteins will have to be produced in mammalian cell lines because of post-translational modification, such as glycosylation, which is difficult to mimic in prokaryotic and lower eukaryotic hosts. In addition, much research on mammalian cells must be performed on mammalian hosts. For these reasons, it is desirable to provide regulatory systems and vectors which are capable of replication and expression in mammalian hosts.

2. Description of the Prior Art

A subgenomic fragment of the bovine papilloma virus (BPV) induces malignant transformation in certain target cells, as reported by: Lowy, et al. (1980) Nature 287:72-74. The BPV subfragment exists as a self-replicating episome in certain hosts as reported by: Law, et al. (1981) Proc. Nat. Acad. Sci USA 78:2722-2731. Chimeric BPV vectors containing various genes can exist in cells as episomes. See, Sarver, et al. (1981) Mol. Cell Biol. 1:486-496 where the cells containing the vector were selected on the basis of their transformed phenotype.

SUMMARY OF THE INVENTION

Novel DNA segments and constructions comprising an inducible, transcriptional regulatory system recognized by mammalian hosts are provided. In particular, the human metallothionein II (hMT-II) transcriptional regulatory system allows for regulated control of expression when stressed by heavy metals or glucocorticoids and can be combined with a variety of DNA sequences, typically structural genes, to provide DNA constructions for regulated transcription and translation of said DNA sequences. The hMT-II regulatory system can be joined to a mammalian extrachromosomal replication system to provide episomal constructions capable of self-replication and inducible expression in mammalian hosts.

BRIEF DESCRIPTION OF THE DRAWINGS

FIG. 1 is a 3.2 kbp HindIII fragment containing the human metallothionein gene.

FIG. 2 is a restriction map of the pMTII-BPV(−) vector.

FIG. 3 is a graph illustrating the cadmium resistance of mouse fibroblast C127 cells transformed with BPV-3 relative to those transformed with pMTII-BPV(−).

DESCRIPTION OF THE SPECIFIC EMBODIMENTS

Methods and compositions are provided for controlled expression of a gene in a mammalian host. DNA sequences which comprise the human metallothionein II (hMT-II) transcriptional regulatory system are employed. The hMT-II regulatory system is inducible by elevated concentrations of heavy metals and glucocorticoids and includes the promoter region (RNA polymerase recognition and binding sites), the transcriptional initiation sequence (cap site), and the regulatory sequence(s) responsible for inducible transcription. The regulatory system is found on a DNA fragment of fewer than about 500 bp (base pairs) located on the 5' flanking region of the hMT-II gene upstream of the translational initiation codon. As used herein, the term upstream means in the direction opposite to transcription, while the term downstream means in the direction of transcription.

The transcriptional regulatory sequences may be combined with an extrachromosomal replication system for a predetermined mammalian host and other DNA sequences having restriction site(s) for insertion of genes under transcriptional control of the regulatory sequences to provide a vector for the regulated transcription and translation of the inserted genes in said mammalian host. The vector can also include a prokaryotic replication system allowing amplification in a prokaryotic host, markers for selection, and other DNA regions.

Alternatively, the subject regulatory system may be joined to a desired structural gene and the resulting DNA construct introduced directly into a mammalian host. Methods for such direct transfer include direct injection of the DNA into nuclei (Cappechi (1980) Cell 22:479-488) and co-transformation by calcium precipitation (Wigler et al. (1979) Cell 16:777-785).

The hMT-II regulatory system can be isolated from the hMT-II gene which is located on a 3.2 kbp (kilobase pair) HindIII fragment of the human genome. (FIG. 1). The entire fragment may be used by introduction into a HindIII insertion site on an appropriate vector. By then inserting the gene to be expressed downstream of the hMT-II translation initiation codon, a fused protein will result. By inserting the gene (having its own start and stop codons) between the hMT-II regulatory system and translation initiation codon, the native polypeptide corresponding to the inserted gene will be expressed.

Alternatively, the 3.2 kbp fragment may be further restricted, particularly at a site within the hMT-II structural gene. The fragment containing the 5' flanking region may then be chewed back using a double stranded exonuclease for a period of time chosen to remove a desired number of base pairs. In this manner, a portion of the fragment downstream from the regulatory region and containing the translation initiation codon may be removed. It is desirable to remove the hMT-II translation initiation codon so that translation of the inserted gene will commence at its own start site. The resulting shortened fragment may then be inserted into the vector using linkers or homopolymer tailing to introduce desired restriction sites compatible with the remaining regions of the vector.

The transcriptional regulatory system will be combined with a terminator for complete transcriptional control of a structural gene. Conveniently, the terminator can be derived from the hMT-II gene, although the terminator of the inserted structural gene may itself carry a suitable terminator. When the intact hMT-II gene is employed, the terminator will naturally be present. When the shortened 5' flanking fragment is employed, as just described, it may be necessary to provide a terminator downstream from the translation termination codon of the inserted structural gene, although usually this will not be necessary where the cleavage site of the hMT-II gene is closer to the 5'-end. The terminator can be obtained from the hMT-II gene by cleaving at a restriction site internal to the gene and isolating the fragment containing the terminator. The terminator fragment may then be joined downstream of the structural gene. Other balanced promoters will also find application.

The extrachromosomal replication system must be capable of replicating in a mammalian host. Suitable replication systems may be derived from papovaviruses, such as simian virus 40 and bovine papilloma virus; adenoviruses; avian retroviruses, such as avian sarcoma virus; and mammalian retroviruses, such as Maloney leukemia virus. Such viral DNA will be suitably modified to prevent cell lysis when introduced to the host. In the case of retroviruses, RNA transcripts of the DNA sequences of the present invention will be employed. Of particular interest are bovine papilloma viruses which are able to exist in certain mammalian hosts as circular episomes at high copy numbers, typically from about 10 to 120 copies per cell.

In addition to the mammalian replication system, it will often be desirable to provide a prokaryotic replication system to allow for amplification of the vector in a bacterial host. This allows large quantities of the vector to be grown in well characterized bacterial systems prior to transforming a mammalian host. Suitable prokaryotic replication systems are well known and include plasmids such as pBR322, pRK290, ColEI, and bacteriophages, e.g., λdv. The prokaryotic replication systems will necessarily include an origin of replication recognizable by a prokaryotic host, and will usually include one or more markers for the selection of transformants in the prokaryotic host. Such markers include biocide resistance and toxin resistance. Alternatively, complementation allowing the growth of an auxotrophic host in a selective medium may be employed. Such techniques are well known in the art and need not be discussed further.

Usually, the markers employed will be different for selection in prokaryotic and eukaryotic hosts. Various dominantly acting markers are useful in mammalian cell lines. They usually comprise a specific gene whose expression confers a new drug-resistant phenotype to the mammalian cells in an appropriate selective medium. Other specific markers include the bacterial xanthine-guanine phosphoribosyl transferase gene which can be selected in medium containing mycophenolic acid and xanthine (Mulligan et al. (1981) Proc. Nat. Acad. Sci. USA 78:2072-2076); vectors carrying a mouse cDNA fragment coding for dihydrofolate reductase may be selected in medium containing aminopterine (Subramani et al. (1981) Mol. Cell Biol. 1:854-861); and a bacterial plasmid gene specifying an aminoglycoside phosphotransferase that inactivates antibacterial action of neomycin-kanamycin derivatives may be selected in medium containing G418, a neomycin derivative toxic for most mammalian cell lines (Colbere-Garapin et al. (1981) J. Mol. Biol. 150:1-14). So long as the vector retains the intact hMT-II structural gene, of course, heavy metal resistance may be used as a selective marker.

In the exemplary method for preparing the vectors of the subject invention, both the mammalian replication system and the hMT-II regulatory system are inserted into a suitable prokaryotic plasmid. The manner and order of the insertion are not critical and it is necessary only that the resulting vector retain viable replication systems for both the prokaryotic and eukaryotic hosts.

The vector so described may be amplified in a suitable prokaryotic host, and the amplified vector may then be isolated and further manipulated as desired. In addition to inserting the structural gene of interest, other functional features such as eukaryotic markers, and the like may be added. Conveniently, the vector is further amplified and purified after each insertion to maintain a suitably large source of the plasmid for further manipulation.

It may be desirable to excise all or part of the hMT-II structural gene from the vector to allow insertion of the structural gene of interest. This may be accomplished by cleaving the gene at an internal restriction site, for example, PvuII and/or BamHI. The resulting linear DNA sequences may then be treated with a double-stranded exonuclease to remove a desired portion of the hMT-II structural gene and allow insertion of the desired structural gene proximate the hMT-II promoter region. The insertion of the desired structural gene is most conveniently accomplished with the use of blunt-ended linkers or homopolymer tailing. The structural gene can be inserted in the proper orientation for expression by employing different linkers at the ends of the gene.

After the hMT-II structural gene has been inactivated, the vector will lose the ability to confer heavy metal resistance. Thus, if it is desired to induce expression of the inserted structural gene with toxic levels of heavy metals, the host will have to be heavy metal resistant. This will usually be the case since metallothioneins are widely distributed in animal and plant cells.

The resulting DNA constructs are useful as cloning vehicles for a structural gene of interest in a mammalian host. The structural gene will be under the control of the hMT-II transcriptional regulatory system, including the promoter, which is inducible by elevated concentrations of heavy metals and glucocorticoid hormones, typically in the range from about $10^{-7}$M to $10^{-2}$M, more usually $10^{-6}$M to $10^{-3}$M, most often $10^{-6}$M to $10^{-4}$M. By such induction, from about 20-50% of the total mRNA of the cell can be derived from the structural gene under the control of the hMT-II regulatory system.

One such construct includes a replication system derived from the bovine papilloma virus and exists in the host as a high copy number (10 to 120) episome which does not integrate into the host chromosome. The structural gene is expressed and regulated in the transformed cells using the hMT-II regulatory system.

A wide variety of structural genes may be introduced into the subject vectors for the production of peptides, such as enzymes, proteins, hormones, novel protein structures and the like. In addition, the subject constructs can be used for the enhanced production of DNA derived from a particular structural gene, for cloning and sub-cloning, as well as for enhanced production of mRNA which can then be used for the production of cDNA. The vectors find wide application because of their versatility in allowing for amplification in bacteria and for replication, transcription, and translation in mammalian cells, which allows for glycosylation, secretion, etc.

The following experiments are offered by way of illustration and not by way of limitation.

EXPERIMENTAL

Materials and Methods

The following abbreviations are used: BPV: bovine papilloma virus; MT: metallothionein; $Cd^r$: cadmium resistance; DME: Dulbeco's modified Eagle medium; FCS: fetal calf serum; PIPES: piperazine-N,N'-bis(2-ethanesulfonic acid); and EDTA: ethylene-dinitrolotetraacetic acid.

1. Cloning of cDNA for the Human MT-II Gene

Total RNA was extracted by the method of Chirgwin et al., (1979) Biochemistry 18:5294–5299, from HeLa cells maximally induced to synthesize metallothionein by incubation in $10^{-5}M$ $CdCl_2$ and $10^{-4}M$ cycloheximide for 8 hr. prior to harvest, Poly(A)-containing RNA was selected by hybridization to oligo(dT) cellulose (Aviv and Leder (1972) Proc. Natl. Acad. Sci USA 72:3961–3965) and used as template for the synthesis of double-stranded cDNA by sequential reverse transcriptase reactions. Following removal of hair-pin loops by $S_1$ nuclease digestion homopolymeric tracts (tails) with an average of 12 dCMP residues were added to the 3' termini of the cDNA by incubation with terminal transferase and dCTP (Chang et al., (1978), Nature 275:617–624). The double stranded, dCMP tailed cDNA sequences were annealed to plasmid pBR322 DNA, previously linearized with restriction endonuclease PstI and 3'-tailed with an average of 10 dGMP residues. The resultant chimeric plasmid DNA was used to transform E. coli strain RRI. The yield of recombinant colonies was $4 \times 10^3/\mu g$ of cDNA, greater than 90% being $Amp^s$, $Tet^r$ phenotype.

Bacterial colonies containing recombinant plasmids were grown and fixed on 0.45 micron nitrocellulose filters essentially as described by Grunstein and Hogness (1975) Proc. Natl. Acad. Sci. USA 72:3961–3965. Duplicate filters were hybridized with $^{32}P$-labelled cDNA synthesized from poly(A)-containing RNA from either (a) induced or (b) uninduced HeLa cells, as described above. Twenty-four colonies were judged by autoradiography to give a stronger hybridization signal with induced cDNA.

Plasmid DNA was prepared from each of these colonies and digested with BamHI and AvaII. Four colonies were found to contain a BamHI site within the cloned insert sequence and also to hybridize relatively strongly with a restriction fragment of a cloned mouse MT-I cDNA (Durnam et al., Proc. Natl. Acad. Sci. USA (1980) 77:6511–6515) containing only coding sequences. The identity of these sequences as coding for human metallothionein was verified by nucleic acid sequence analysis. Further restriction endonuclease analysis of these plasmids revealed the presence of a PvuII site within the cloned cDNA sequence. A BamHI-PvuII restriction fragment containing only human MT-II coding sequences from phMTII-3 was nick-translated (Rigby et al., (1977) J. Mol. Biol. 113:237–251) to provide the probe used hereinafter.

2. Construction of the MTII-BPV Vector

Restriction enzymes were used according to manufacturers recommendations (Bethesda Research Laboratories). A 3.2 kbp, HindIII fragment of human genomic DNA prepared from white blood cells and containing the human MT-II gene and 0.8 kbp of the 5' flanking region was isolated by electrophoresis on 1% agarose gel and electroelution. See FIG. 1 where the exons are indicated by solid black regions. pBPV DNA (available from Dr. P. Gruss, National Institutes of Health) was linearized with HindIII, dephosphorylated and ligated to the MT-II HindIII fragment. Recombinant plasmids were used to transform E.coli K-12 host (strain RRI). The desired recombinants were identified by restriction enzyme analysis of plasmid DNA isolated from individual colonies (Holmes and Quigley (1981) Anal. Biochem. 114:193–197). See FIG. 2. All recombinant DNA procedures were performed according to National Institutes of Health guidelines.

3. Transformation and Selection of Cadmium Resistant Cells

Calcium phosphate coprecipitate of vector DNA and carrier salmon sperm DNA was prepared as described by Wigler et al., supra. Mouse C127 cells (available from Dr. P. Gruss) (at a density of $10^6$ cells/100 mm plate) were incubated with the precipitate for 16–18 hrs., and for additional 48 hrs. with normal growth medium: DME+10% FCS. Selection was in medium containing 20 $\mu$M $CdCl_2$ and 20 $\mu$M $ZnCl_2$. Surviving colonies reached a size allowing isolation and propagation into mass cultures in about 2 weeks.

4. Preparation of Cellular RNA and DNA and their Analyses

Cells were harvested by trypsinization and lysed with NP40 as described by Anderson et al. (1979) Proc. Nat. Acad. Sci. USA 71:2756–2761. Nuclei were pelleted by centrifugation in an Eppendorf microfuge and used for DNA isolation. Supernatants were extracted three times with phenol-chloroform isoamylalcohol (24:24:1) mixture and RNA was collected by ethanol precipitation. High molecular weight DNA was prepared from nuclei as described by Bell et al. (1981) Proc. Nat. Acad. Sci. USA 78:5759–5763. DNA and RNA concentrations were determined by optical density measurements. RNA was glyoxalated, separated on 1.5% agarose gels and transferred onto nitrocellulose filters as described by Southern (1975) J. Mol. Biol. 98:503–517. Probes based on the BamHI-PvuII coding region of phMT-II (Section 1, above) were labelled by nick translation (Rigby et al. (1977) J. Mol. Biol. 113:237–251) to a specific activity of $10^8$ CPM/$\mu$g DNA. Hybridization and washing was as described by Wahl et al. (1979) Proc. Nat. Acad. Sci. USA 76:3683–3687.

5. Nuclease Mapping Procedure

A modification of the Weaver and Weissman method (1979) Nuc. Acids. Res. 5:1175–1193 was used. The probe used was the HindIII-BamHI fragment containing the 5' end of the MT-II gene (see FIG. 1) which was end labelled at the BamHI site using $T_4$ polynucleotide kinase (PL Biochemicals) and $[\alpha^{32}P]$-ATP (Amersham, <3000 Ci/mmol). Total cytoplasmic RNA 50–150 $\mu$g was hybridized to the probe (50,000 CPM) in 30 $\mu$l of 80% formamide, 0.4M NaCl, 40 mM PIPES pH 6.5 1 mM EDTA for 12 hrs. at 54° C. under paraffin oil. The hybridization mixture was diluted into 370 $\mu$l of ice cold 30 mM Na acetate pH 4.6, 0.25M NaCl, 1 mM $ZnCl_2$, 5% glycerol and digested with 360 units of mung bean nuclease (PL Biochemicals) for 90 min. at 37° C. The digestion was terminated by phenol-chloroform extraction and the nucleic acids isolated by ethanol precipitation. The pellet was resuspended in 60 $\mu$l of 0.2N NaOH and incubated for 60 min. at 45° C. 10 $\mu$l of 1M Tris-Cl pH 7.5 and 60 $\mu$l of 0.2N HCl were added and the remainder of the nucleic acid was isolated by ethanol precipitation. It was resuspended in 10 $\mu$l of formamide dye mix and analyzed on 8% sequencing gels. Chemical degradation reactions were performed as described by Maxam and Gilbert (1980) Methods Enzymol. 65:99–599.

RESULTS

A plasmid vector designated pMTII-BPV(−) (FIG. 2) was constructed with the MT-II gene in the reverse orientation (counter-clockwise in FIG. 2) relative to the direction of transcription of the BPV-1 subgenomic fragment (clockwise in FIG. 2). Such arrangement should minimize readthrough transcription of MT-II mRNA from the BPV promoters.

The vector pMTII-BPV(−) was digested with SalI prior to transfection to achieve physical separation of the fragment containing the MTII-BPV sequences from the pBR322 sequences. Mouse fibroblast C127 cells were then transfected with the SalI digested pMTII-BPV(−) DNA, with SalI digested pBPV$_{69T}$ serving as a control. Forty-eight hours after transfection, the cells were subjected to selection in medium containing 20 μM Cd$^{++}$ and 20 μM Zn$^{++}$. Cadmium resistant (Cd$^r$) colonies were first observed 10-14 days after transfection of cells with pMTII-BPV(−) DNA. Cultures transfected with pBPV$_{69T}$ did not give rise to any surviving colonies and by one week after the start of selection were all dead. The yield of cadmium resistant colonies was approximately 80–100 per microgram of DNA. This number is only slightly lower than the number of transformed loci generated by the same vector (approximately 150 per microgram of DNA). Examination of the Cd$^r$ colonies indicated that all of them had a transformed phenotype.

Several of the Cd$^r$ colonies were picked and propagated into mass cultures. They all retained the Cd$^r$ phenotype. Three of those clones, designated C127 CdR14, C127 CdR15 and C127 CdR18 were characterized in greater detail than the others.

To determine the extent of cadmium resistance of the Cd$^r$, relative to BPV transformed C127 cells (clone BPV-3) a colony formation assay was used. Cd$^r$ C127 (CdR14) and BPV transformed cells were plated in various dilutions (10$^4$, 10$^3$, and 10$^2$ cells/plate) on 100 mm plates and were allowed to form colonies in the presence of different cadmium concentrations. The cells were maintained in DME+10% FCS with the indicated Cd$^{++}$ concentration for two weeks. The number of colonies formed were determined by staining with Geimsa stain after fixing with ethanol:acetic acid (3:1). The number of surviving colonies was derived in comparison to a 0 Cd$^{++}$ control. See FIG. 3.

Control plating efficiency was identical for both cell types (70–72%). The BPV3 cells were very sensitive to cadmium and the number of surviving colonies dropped down to 10% of the control value, at 4 μM Cd$^{++}$. At that Cd$^{++}$ concentration the Cd$^r$ cells were not affected. Their relative plating efficiency dropped to 10% of control, only at 80 μM Cd$^{++}$. Based on this criterion, Cd$^r$ cells generated by transformation with pMTII-BPV(−) are 20 fold more resistant than BPV transformed cells.

It was determined that the acquisition of cadmium resistance by the cells transformed with pMTII-BPV(−) was the result of expression of human MT-II gene. Four Cd$^r$ clones (CdR14) were grown in the presence of cadmium concentrations of 10, 35, 100 and 350 μM, for 24 hours. At the end of this induction period, cytoplasmic RNA was extracted and analyzed for presence of human MT-II mRNA by Southern blot hybridization as described in Materials and Methods. On the same gel, 20 μg of total cellular DNA from Cd$^{++}$ induced HeLa cells and Cd$^{++}$ induced BPV transformed C127 cells were analyzed. The probe used was the 5′ noncoding region of the human MT-II cDNA, prepared as described in Materials and Methods, which does not hybridize to mouse MT mRNA.

The four CdR14 clones produced mature MT-II mRNA identical in size to the human MT-II mRNA expressed in HeLa cells. The C127 cells transformed with BPV did not. Moreover, the level of expression of the CdR14 clones was regulated by the concentration of Cd$^{++}$ in the growth medium. Two other Cd$^r$ clones tested (CdR15 and CdR18) exhibited identical levels of expression and dose-response relationship.

The observed induction of human MT-II mRNA appears to result from increased transcriptional activation rather than higher gene concentration. The copy numbers of the MT-II gene in cells subjected to different induction conditions were compared. There was no observed effect of Cd$^{++}$ concentration on MT-II gene copy number.

The start sites of transcription of the MT-II gene carried on the BPV vector in mouse cells were determined using the nuclease mapping technique described in Materials and Methods and were compared to the start sites of transcription of the gene in its natural chromosomal environment.

The coding strand of the MT-II gene was labelled at the 5′ distal BamHI site (FIG. 1). The BamHI-HindIII fragment containing 876 nucleotides of 5′ flanking region was isolated to be used as a hybridization probe. It was hybridized to total cytoplasmic RNA (60 μg) from either C127 Cd$^r$ cells (grown for 24 hours in 50 μM Cd$^{++}$) or cadmium induced HeLa cells.

After digestion with mung bean nuclease, the sizes of the protected DNA fragments were determined by electrophoresis on 8% sequencing gels, using sequencing ladders produced by chemical degradation of the BamHI-HindIII fragment as size markers, as described in Materials and Methods. Hybridization of the BamHI-HindIII fragment to RNA from HeLa cells yielded three protected DNA fragments stretching from the BamHI site to the T residue at −3, the A residue at +1, and the A residue at +3. Hybridization of the probe to RNA from Cd$^r$ C127 cells (clone CdR15) resulted in two protected bands, corresponding to fragments starting at the BamHI site and ending at the A residues. These results indicate that two of the authentic start sites of transcription of the human MT-II gene are used in mouse cells in which the gene is present on an episome.

It was determined that cells selected by cadmium resistance contained free copies of the vector. Total cellular DNA 10 μg was prepared from several Cd$^r$ clones (CdR14 and CdR15), digested with restriction endonuclease EcoRI, separated on 1% agarose gels and analyzed by Southern blot hybridization. $^{32}$P-labelled pBPV$_{69T}$ was used as a probe to detect the fragments containing MTII-BPV sequences.

Cd$^r$ cells were found to contain about 20 copies of the vector. The vector DNA is not integrated into the genomic DNA. In undigested DNA samples, MTII-BPV sequences are present as catenated circles and migrate as a high molecular weight complex. Mechanical shearing releases form I and form III DNA from those complexes. Digestion of DNA with a restriction enzyme that cuts only once within the vector (e.g. EcoRI) generates full length linear molecules. The size of the bands observed (9.1 Kbp) corresponds to the calculated size of the large SalI fragment of pMTII-BPV(−) containing the BPV subgenomic transforming fragment, the MT-II gene and 600 bp of pBR322 (see FIG. 2).

Since the cells were originally transformed with a SalI digest of pMTII-BPV(−), and not with a purified MTII-BPV fragment, they were found to contain a few integrated copies of the pBR322 fragment due to cotransfer. Those fragments can be detected as faint bands when a probe containing pBR322 sequences is used.

No religation of the two SalI fragments occurred in the cells. While the large fragment containing the MT-II gene and the BPV sequences was recircularized and continued to replicate as an episome, the smaller SalI fragment, consisting only of pBR322 DNA integrated into multiple sites in the host DNA.

In accordance with the subject invention, a hybrid DNA sequence is provided which yields efficient transformation of a mammalian host and high levels of expression of a structural gene within the host. In particular, the human MT-II gene has been cloned and, together with the associated promoter region, has been inserted into a bovine papilloma virus vector. The promoter is inducible by elevated cadmium levels allowing amplified expression of the associated structural gene. The resulting vector has been characterized and, by conventional techniques, other structural genes may be inserted along with or in place of the MT-II structural gene. Thus, the DNA sequence can act as a general cloning vehicle for expression of a variety of genes. Moreover, the promoter region itself is useful generally to maximize expression of genes in mammalian cells.

Although the foregoing invention has been described in some detail by way of illustration and example for purposes of clarity and understanding, it will be obvious that certain changes and modifications may be practiced within the scope of the appended claims.

What is claimed is:

1. A DNA sequence of less than 500 base pairs, said DNA sequence comprising the human MT-II transcriptional regulatory system further comprising the transcription initiation sequence.

2. A DNA sequence as in claim 1, further comprising the human MT-II translation initiation codon located downstream from the transcription initiation sequence in the direction of transcription.

3. A DNA sequence as in claim 1, further comprising the human MT-II transcription termination sequence downstream from the transcription initiation sequence and at least one restriction site intermediate said transcription initiation sequence and said transcription termination sequence.

4. A DNA sequence as in claim 3, further comprising a structural gene other than human MT-II inserted at said restriction site.

5. A DNA construct capable of regulated expression of an inserted gene in a mammalian host, said construct comprising an extrachromosomal replication system recognized by a mammalian host, which replication system has been joined to a human MT-II gene inducible regulatory system in vitro, said construct having DNA sequence(s) defining at least one restriction site within the transcriptional control of the regulatory region for insertion of the gene.

6. A DNA construct as in claim 5, wherein the mammalian extrachromosomal replication system is derived from a papovavirus.

7. A DNA construct as in claim 6, wherein the papovavirus is bovine papilloma virus.

8. A DNA construct as in claim 5, further comprising a prokaryotic replication system.

9. A DNA construct as in claim 8, wherein the prokaryotic replication system is derived from pBR322.

10. A DNA construct useful for expression of a structural gene to produce a polypeptide in a mammalian host, said vector comprising (a) a replicon from bovine papilloma virus and (b) a regulatory system from a human MT-II gene comprising a promoter and a terminator and having at least one restriction site downstream from the promoter in the direction of transcription.

11. A DNA construct as in claim 10, wherein the regulatory system is derived from the human MT-II gene and the restriction site is in the structural region of said MT-II gene.

12. A DNA construct as in claim 10, further comprising a structural gene inserted into the restriction site so that expression of the structural gene is under the regulatory control of the promoter and terminator.

13. A mammalian cell transformed with at least one DNA construct according to claim 12.

14. A mouse fibroblast cell transformed with at least one DNA construct according to claim 12.

15. A method for producing a polypeptide encoded by a structural gene, said method comprising:
    transforming a mammalian cell with a DNA construct according to claim 12;
    growing the transformed cell in an appropriate nutrient medium;
    inducing expression of the structural gene by the addition of a heavy metal or a glucocorticoid to the nutrient medium; and
    isolating the polypeptide.

16. A method as in claim 15, wherein the mammalian cell is a mouse fibroblast.

* * * * *